United States Patent
Chen

(10) Patent No.: US 10,889,797 B2
(45) Date of Patent: Jan. 12, 2021

(54) THREE PHASE PARTITIONING (TPP) METHOD FOR VIRUS PURIFICATION

(71) Applicant: Virovek, Inc., Hayward, CA (US)

(72) Inventor: Haifeng Chen, Piedmont, CA (US)

(73) Assignee: Virovek Incorporation, Hayward, CA (US)

( * ) Notice: Subject to any disclaimer, the term of this patent is extended or adjusted under 35 U.S.C. 154(b) by 91 days.

(21) Appl. No.: 16/203,055

(22) Filed: Nov. 28, 2018

(65) Prior Publication Data

US 2019/0161725 A1   May 30, 2019

Related U.S. Application Data

(60) Provisional application No. 62/591,383, filed on Nov. 28, 2017.

(51) Int. Cl.
| | |
|---|---|
| *C12N 1/02* | (2006.01) |
| *C12N 1/04* | (2006.01) |
| *C12N 5/07* | (2010.01) |
| *C12N 1/06* | (2006.01) |
| *C12N 7/00* | (2006.01) |

(52) U.S. Cl.
CPC ........ *C12N 1/02* (2013.01); *C12N 1/04* (2013.01); *C12N 1/06* (2013.01); *C12N 5/0601* (2013.01); *C12N 7/00* (2013.01); *C12N 2750/14151* (2013.01)

(58) Field of Classification Search
None
See application file for complete search history.

(56) References Cited

U.S. PATENT DOCUMENTS

| 7,439,337 B2 | 10/2008 | Ward |
| 9,771,401 B2 | 9/2017 | Tota |

FOREIGN PATENT DOCUMENTS

| WO | 2010/046920 A1 | 4/2010 |
| WO | 2010/074465 A1 | 7/2010 |

OTHER PUBLICATIONS

Gagaoua et al., BIOSENS vol. 5, issue 1, 5 pages. (Year: 2016).*
Yan et al., Critical Reviews in Food Science and Nutrition vol. 58, No. 14, 2416-2431 (Year: 2018).*
Alici, E. H. & Arabaci, G., Purification of polyphenol oxidase from borage (*Trachystemon orientalis* L.) by using three-phase partitioning and investigation of kinetic properties., Int. J. Biol. Macromol., 2016, 93, 1051-1056.
Brument, N., et al., A versatile and scalable two-step ion-exchange chromatography process for the purification of recombinant adeno-associated virus serotypes-2 and -5., Molecular Therapy, 2002, 6, 5, 678-686.
Chen, H., Manufacturing of adeno-associated viruses, for example: AAV2., Methods Mol. Biol., 2011, 737, 235-246.
Chen, H., Exploiting the Intron-splicing Mechanism of Insect Cells to Produce Viral Vectors Harboring Toxic Genes for Suicide Gene Therapy.. Mol. Ther. Nucleic Acids, 2012, 1, e57.
Duman, Y. A. & Kaya, E., Three-phase partitioning as a rapid and easy method for the purification and recovery of catalase from sweet potato tubers (Solanum tuberosum)., Appl. Biochem. Biotechnol., 2013, 170, 1119-1126.
Gagaoua, M., et al., Three phase partitioning, a scalable method for the purification and recovery of cucumisin, a milk-clotting enzyme, from the juice of *Cucumis melo* var. *reticulatus*., Int. J. Biol. MacromoL, 2017, 102, 515-525.
Gagaoua, M. and Hafid, K., Three Phase Partitioning System, an Emerging Non-Chromatographic Tool for Proteolytic Enzymes Recovery and Purification, Biosens. J., 2016, 5, 1.
Gagaoua, M., et al., Data in support of three phase partitioning of zingibain, a milk-clotting enzyme from Zingiber officinale Roscoe rhizomes, Data in Brief, 2016, 6, 634 639.
Guo, P, et al., A simplified purification method for AAV variant by polyethylene glycol aqueous two-phase partitioning, Bioengineered, 2013, 4, 2, 103-106.
Maxwell, S.A., et al., Solubilization of SV40 plasma-membrane-associated large tumor antigen using single-phase concentrations of 1-butanol., Mol. Carcinog. 1989, 2, 322-335.
Negrete, A., et al. Aqueous two-phase recovery of bio-nanoparticles: a miniaturization study for the recovery of bacteriophage T4., J Chromatogr. B. Analyt. Technol. Biomed. Life Sci., 2007, 854, 13-19.
Pike, R.N. and Dennison C., Protein Fractionation by Three Phase Partitioning (TPP) in Aqueous /t-Butanol Mixtures, Biotechnology and Bioengineering, 1989, 33, 221-228.
Sagu, S. T., et al., Extraction and purification of beta-amylase from stems of Abrus precatorius by three phase partitioning., Food Chem., 2015, 183, 144-153.
Szermer-Olearnik, B. and Boratyński, J., Removal of endotoxins from bacteriophage preparations by extraction with organic solvents., PLoS ONE, 2015, 10, 3, e0122672.
Tomono, T., et al., Ultracentrifugation-free chromatography-mediated large-scale purification of recombinant adeno-associated virus serotype 1 (rAAV1)., Mol Ther Methods Clin Dev., 2016, 3, 15058.

(Continued)

*Primary Examiner* — Shanon A. Foley
*Assistant Examiner* — Myron G Hill
(74) *Attorney, Agent, or Firm* — Zackson Law LLC; Saul L. Zackson

(57) ABSTRACT

Methods of purifying a virus from a virus-infected cell lysate using three-phase partitioning (TPP) are disclosed. The methods comprise a first round of TPP, including mixing a cell lysate comprising a virus with ammonium sulfate and t-butanol, and separating the mixture, thereby forming a first aqueous phase, a first organic phase, and a first interphase. The first aqueous phase can comprise the virus, which can be subjected to a second round of TPP, resulting in a second aqueous phase, a second organic phase, and a second interphase. The second interphase can comprise highly purified virus. The methods can comprise subjecting a first aqueous phase to further purification by column chromatography or density gradient centrifugation. Purification of AAV, including AAV2, AAV5 and AAV6, from lysates of infected insect cell cultures is demonstrated. TPP-purified AAV particles infect at least as well as those prepared by standard methods.

24 Claims, 11 Drawing Sheets

(56) References Cited

OTHER PUBLICATIONS

Ward, W.W., Three-Phase Partiioning for Protein Purification, Innovations in Pharmaceutical Technology, 28-34, 2009.
Hermens, W.T.., et al., Purification of Recombinant Adeno-Associated Virus by Iodixanol Gradient Ultracentrifugation Allows Rapid and Reproducible Preparation of Vector Stocks for Gene Transfer in the Nervous System, Human Gene Therapy., 2004, 10, 1885-1891.
Yan, J. K., et al., Three-phase partitioning as an elegant and versatile platform applied to nonchromatographic bioseparation processes., Crit. Rev. Food Sci. Nutr., 2017, 58, 14, 2416-2431.
Zolotukhin, S., et al., Recombinant adeno-associated virus purification using novel methods improves infectious titer and yield., Gene Therapy, 1999, 6, 973-985.
Guo, P., et al., Rapid and simplified purification of recombinant adeno-associated virus, Journal of Virological Methods, 183, 2,Apr. 18, 2012 (Apr. 18, 2012), pp. 139-146.
Dennison, C., et al., Three Phase Partitioning: Concentration and Purification of Proteins, Protein Expression and Purificat, 11, 2,Nov. 1, 1997 (Nov. 1, 1997), pp. 149-161.
Kulkarni, V.M., et al., Extraction of mangiferin from Mangifera indica leaves using three phase partitioning coupled with ultrasound, Industrial Crops and Products., 52, Jan. 1, 2014 (Jan. 1, 2014), pp. 292-297.

\* cited by examiner

THREE PHASE PARTITIONING (TPP) METHOD FOR VIRUS PURIFICATION

REFERENCE TO PRIOR APPLICATION

This application claims benefit of and priority to U.S. Provisional Application 62/591,383 filed on Nov. 28, 2017. Application 62/591,383 is incorporated by reference in its entirety.

INTRODUCTION

This disclosure is in the field of virus purification, in particular purification of a non-enveloped virus such as adeno-associated virus grown in vitro.

Recombinant adeno-associated virus (AAV) vector has emerged as a versatile and effective gene therapy delivery vehicles. However, purification of AAV by column chromatography (e.g., Brument, N., et al., Molecular Therapy 6, 678-686, 2002) is expensive and complicated. Gradient centrifugation methods of AAV purification using cesium chloride or iodixanol (e.g., Wim, T., et al., Human Gene Therapy. July 2004, 10(11): 1885-1891; Zolotukhin, S., et al., Gene Therapy (1999) 6, 973-985, 1999) are difficult to scale up due to the small capacity of centrifuge tubes. Polyethylene glycol (PEG)/aqueous two phase-partitioning methods (e.g., Guo, P, et al., Bioengineered, 4:2, 103-106, DOI: 10.4161/bioe.22293) yield limited amounts of AAV vectors.

Three phase partitioning (TPP) is a non-chromatographic technology for the separation of bioactive proteins from natural sources (Yan, J. K., et al., Crit. Rev. Food Sci. Nutr., 2017, 1-16.) Recently it has been used as a scalable method for purification of several proteins (Duman, Y. A. & Kaya, E., Appl. Biochem. Biotechnol., 2013, 170, 1119-1126; Gagaoua, M., et al., Int. J. Biol. Macromol., 2017, 102, 515-525; Alici, E. H. & Arabaci, G., Int. J. Biol. Macromol., 2016, 93, 1051-1056; Sagu, S. T., et al., Food Chem., 2015, 183, 144-153) and viral antigens (Maxwell, et al., Mol. Carcinog. 1989, 2, 322-335; Ward, W. W., Innovations in Pharmaceutical Technology, 28-34, 2009. U.S. Pat. No. 7,439,337 to Ward., W. W.). TPP is based on the use of an organic solvent, usually tertiary butanol (t-butanol) and a salt, usually ammonium sulfate, to precipitate proteins from aqueous solution. Tertiary butanol and similar solvents are normally completely miscible with water, but upon addition of a salt such as ammonium sulfate, a mixture of the aqueous and organic solvents can separate into two phases, a lower aqueous phase and an upper organic (t-butanol) phase. If protein is present in the original aqueous sample, a third phase ("interphase") comprising the protein can form between the lower aqueous and upper t-butanol phase, depending on the concentration of ammonium sulfate added TPP has been used to purify several proteins, but there have been no reports of the use of TPP to purify virus particles such as AAV particles.

Negrete, A., et al. (J Chromatogr. B. Analyt. Technol. Biomed. Life Sci., 2007, 854, 13-19) describe aqueous recovery of bacteriophage using PEG detergent systems, but do not disclose the use of organic solvents. Szermer-Olearnik, B. and Boratyfski, J. (PLoS ONE, 2015, 10, e0122672) describe the isolation of bacteriophage using 1-butanol, but this isomer of butanol is not miscible in water and therefore is not suitable for TPP.

Simple and scalable methods of virus purification are still needed.

SUMMARY

The current inventor has developed methods of purifying virus particles such as AAV particles from crude cell lysates using three-phase partitioning (TPP).

In some embodiments, methods are disclosed of purifying a virus from lysates of a cell culture. The methods all involve at least one round of three-phase partitioning (TPP).

In various configurations, a method of the present teachings can comprise a) forming a first (or only) composition comprising i) a cell lysate comprising a virus, ii) ammonium sulfate, and iii) t-butanol; b) agitating the first (or only) composition, e.g., by shaking, thereby forming a first (or only) mixture, c) separating the first (or only) mixture into a first (or only) aqueous phase, a first (or only) interphase and a first (or only) organic phase; and d) collecting the first (or only) aqueous phase. In various configurations, the ammonium sulfate can be at a first (or only) concentration in which t-butanol is immiscible with water. In various configurations, the aqueous phase can comprise the virus with reduced impurities such as cell debris and cell protein compared to the lysate. In various configurations, the virus can be any virus that can be grown in vitro, or any non-enveloped virus that can be grown in vitro. Non-limiting examples of a non-enveloped virus include a virus from the families Picornaviridae (e.g. Enterovirus, rhinovirus, hepatovirus, cardiovirus, aphthovirus, poliovirus, parechovirus, erbovirus, kobuvirus, teschovirus, or coxsackie virus), Parvoviridae (e.g., Parvovirus B19, canine parvovirus, or human bocavirus), Anelloviridae (e.g. Torque teno virus), Papovaviridae (e.g., Papillomavirus, polyomaviridae, simian vacuolating virus), Adenoviridae (e.g., Adenovirus, Adeno-associated virus, Infectious canine hepatitis virus), Reoviridae (e.g., Reovirus, rotavirus), Caliciviridae (e.g., Norwalk virus, Calicivirus), Astroviridae (e.g., Astrovirus), Caulimoviridae (e.g., cauliflower mosaic virus), Circoviridae, Birnaviridae, or Potyviridae, (potyvirus barley yellow mosaic virus). In some aspects, a virus that can be isolated by a method of the present teachings can be an adenovirus or an adeno-associated virus (AAV), such as, for example, an AAV2, an AAV5 or an AAV6.

In various configurations, a cell lysate can be a cell lysate of virus-infected insect cells such as, without limitation, Sf9 cells infected with an AAV, or virus-infected mammalian cells such as, without limitation, AAV-infected HEK293 cells. In various configurations, in a TPP procedure of the present teachings, ammonium sulfate can be added to a sample comprising a virus, followed by addition of t-butanol.

In various configurations of methods of the present teachings, in the first (or only) round of TPP, the amount of ammonium sulfate that can be added to a sample comprising a virus can be from about 10% to about 30% saturation, or from 10% to 30% saturation. In various configurations, the amount of ammonium sulfate that can be added to a sample comprising a virus in a first or only round of TPP can be about 10%, 10%, about 15%, 15%, about 20%, 20%, about 25%, 25%, about 30% or 30% saturation. In some configurations, when the virus is an AAV2, in the first (or only) round of TPP, the first (or only) ammonium sulfate concentration can be from about 10% to about 25% saturation, or from 10% to 25% saturation. In various configurations, when the virus is an AAV2, in the first (or only) round of TPP, the first (or only) ammonium sulfate concentration can be about 10%, 10%, about 15%, 15%, about 20%, 20%, about 25% or about 25% saturation. In some configurations, when the virus is an AAV5, in the first (or only) round of TPP, the first (or only) ammonium sulfate concentration can be from about 10% to about 20% saturation, or from 10% to 20% saturation. In some configurations, when the virus is an AAV5, in the first (or only) round of TPP, the first (or only) ammonium sulfate concentration can be about 10%, 10%, about 15%, 15%, about 20% or 20% saturation. In some configurations, when the virus is an AAV6, in the first (or only) round of TPP, the first (or only) ammonium sulfate concentration can be from about 15% to about 30% saturation, or from 15% to 30% saturation. In various configurations, when the virus is an AAV6, in the first (or only) round of TPP, the first (or only) ammonium sulfate concentration can be about 15%, 15%, about 20%, 20%, about 25%, 25%, about 30%, or 30% saturation.

In various configurations, the methods can comprise forming a composition by adding ammonium sulfate to a sample comprising a virus, then adding the t-butanol. In various aspects, the volume of t-butanol can be approximately the same as that of the sample. A composition comprising the sample, the ammonium sulfate and the t-butanol can then be agitated to form a mixture.

In various configurations, agitating the composition to form a mixture can comprise shaking the composition.

In various configurations, agitating the composition to form a mixture can comprise vigorously shaking the composition.

In various configurations, following the agitating, a mixture can separate spontaneously into at least three layers, i.e., an organic phase, an interphase and an aqueous phase, by settling of the mixture.

In various configurations, such a three-phase arrangement can form by settling for at least 30 minutes, or for about 30 to about 60 minutes, after the forming of the first (or only) mixture. In various aspects, a first interphase can comprise, consist essentially of, or consist of a loose, spongy mass.

In various configurations, a TPP method of the present teachings, in addition to or instead of settling, can comprise subjecting an agitated first (or only) mixture to centrifugation, thereby accelerating or promoting the separation of the first (or only) mixture into an aqueous phase, an organic (t-butanol) phase and an interphase. In some aspects, a first interphase can comprise, consist essentially or, or consist of a semi-solid spongy layer, and centrifugation can promote its formation.

In some configurations, the centrifuging of a mixture of the present teachings can comprise centrifuging the mixture at about 4000 rpm (about 4293×g) for about 10 min.

In some configurations, the centrifugation can comprise centrifuging a mixture of the present teachings at 3000 rpm to 5000 rpm (approx. 2400×g to 6700×g) for from about 5 minutes to about 10 minutes.

In various embodiments, a first TPP separation procedure of a virus-infected cell lysate can lead to the first aqueous phase comprising the majority of the virus. This first aqueous phase can be collected, and the virus contained therein can be used or further purified. In some configurations, the first interphase can comprise, consist essentially of, or consist of cellular proteins, DNA, and other cell components.

In some configurations, methods of the present teachings can further comprise a second round of TPP, which can comprise e) forming a second composition comprising i) a first aqueous phase collected in d), ii) ammonium sulfate at a second concentration in which t-butanol is immiscible with water, and iii) t-butanol. In various configurations, the second composition can be agitated, thereby forming a second mixture. In various aspects, after the agitating, the second mixture can be separated into at least three phases, including a second organic phase, a second interphase, and a second aqueous phase. In various aspects, the second interphase, which can comprise the majority of the virus, can be collected. In some configurations, in a method of these aspects, the concentration of ammonium sulfate in step e) can be from about 25% to about 40% saturation, or can be from 25% to 40% saturation. In various configurations, in a method of these teachings, the concentration of ammonium sulfate in step e) can be about 25%, 25%, 30%, about 30%, 35%, about 35%, about 40%, or 40% saturation. In some configurations, when the virus is an AAV2, the second ammonium sulfate concentration in step e) can be from about 35% to about 40% saturation, or can be from 35% to 40% saturation. In various configurations, when the virus is an AAV2, the second ammonium sulfate concentration in step e) can be about 35%, 35%, about 36%, 36%, about 37%, 37%, about 38%, 38%, about 39%, 39%, about 40% or 40% saturation. In some configurations, when the virus is an AAV5, the second ammonium sulfate concentration in step e) can be from about 35% to about 40% saturation, or can be from 35% to 40% saturation. In various configurations, when the virus is an AAV5, the second ammonium sulfate concentration in step e) can be about 35%, 35%, about 36%, 36%, about 37%, 37%, about 38%, 38%, about 39%, 39%, about 40% or 40% saturation. In some configurations, when the virus is an AAV6, the second ammonium sulfate concentration in step e) can be from about 30% to about 35% saturation, or can be from 30% to 35% saturation. In various configurations, when the virus is an AAV6, the second ammonium sulfate concentration in step e) can be about 30%, 30%, about 31%, 31%, about 32%, 32%, about 33%, 33%, about 34%, 34%, about 35% or 35% saturation.

In some configurations, after the agitating, the second mixture can be separated into at least three phases by settling, e.g., for about 30 minutes to about 60 minutes. In some configurations, the second mixture can be separated into at least three phases by a second centrifugation in addition to or instead of a second settling. In various aspects, a second centrifugation can comprise centrifuging the second mixture at about 4293×g (about 4000 rpm) for about 10 min, or centrifuging the second mixture at 4293 (4000 rpm) for 10 min, or centrifuging the second mixture at 3000 rpm to 5000 rpm (approx. 2400×g to 6700×g) for 5 minutes to 10 minutes. In various configurations, a second interphase can comprise, consist essentially of, or consist of a loose, spongy mass. This second interphase can comprise the majority of the virus particles, and can be substantially purer than the cell lysate. In some configurations, AAV particles collected from a second interphase after two rounds of TPP can infect target cells at least as well as AAV particles prepared by standard methods.

In some configurations, methods of virus purification of the present teachings can further comprise subjecting virus collected in an aqueous phase in step d) after one round of TPP as described supra to further purification in a column chromatography purification procedure. A column chromatography purification procedure can be, for example and without limitation, a heparin affinity chromatography, a HPLC heparin affinity chromatography, an HPLC cation exchange chromatography, or a combination thereof. (Zolotukhin, S., et al., Gene Therapy 6, 973-985, 1999.) In some configurations, a column chromatography purification procedure can be, for example and without limitation, an ion-exchange chromatography procedure, a gel filtration chromatography procedure, or a combination thereof. (Tomono, T., et al., Molecular Therapy—Methods & Clinical Development 3, 15058, 2016.)

In some configurations, methods of virus purification of the present teachings can further comprise subjecting virus collected in an aqueous phase in step d) after one round of TPP as described supra to further purification in a density gradient centrifugation procedure. In various aspects, a density gradient purification procedure can comprise, for example and without limitation, a sucrose density gradient purification procedure, a cesium chloride density gradient purification procedure, an iodixanol density gradient procedure, or a combination thereof.

The present disclosure includes, without limitation, the following aspects.

In some embodiments of the present teachings, a method of purifying a virus from a virus-infected cell lysate can comprise a) forming a first composition comprising i) a cell lysate comprising a virus, ii) ammonium sulfate and iii) t-butanol; b) agitating the first composition thereby forming a first mixture; c) separating the first mixture to form a first organic phase, a first interphase, and a first aqueous phase; and d) collecting the first aqueous phase, wherein the first aqueous phase comprises the virus, and wherein the ammonium sulfate is at a first concentration in which t-butanol is immiscible with water.

In some configurations, the virus can be selected from the group consisting of an adenovirus and an adeno-associated virus (AAV). In some configurations, the virus can be an adeno-associated virus selected from the group consisting of AAV2, AAV5 and AAV6.

In various configurations of a method of the present teachings the first concentration of ammonium sulfate can be from 10% to 30% saturation. In various configurations, the virus can be an AAV2 and the first ammonium sulfate concentration can be from 10% to 25% saturation. In various configurations, the virus can be an AAV5 and the first ammonium sulfate concentration can be from 10% to 20% saturation. In various configurations, the virus can be AAV6 and the first ammonium sulfate concentration can be from 15% to 30% saturation.

In various configurations of a method of the present teachings, the separating the first mixture can comprise settling the first mixture for at least 30 minutes. In various configurations, the separating the first mixture can comprise settling the first mixture for about 30 to about 60 minutes. In various configurations, the separating the first mixture comprises centrifuging the first mixture. In some configurations, the centrifuging the first mixture comprises centrifuging the first mixture at about 4000 rpm (about 4293×g) for about 10 min.

In various configurations, a method in accordance with the present teachings can further comprise e) forming a second composition comprising i) the first aqueous phase collected in d), ii) ammonium sulfate at a second concentration in which t-butanol is immiscible with water, and iii) t-butanol; f) agitating the second composition thereby forming a second mixture; g) separating the second mixture to obtain a second organic layer, a second interphase, and a second aqueous layer; and h) collecting the second interphase. In some configurations, the second ammonium sulfate concentration can be from 25% to 40% saturation. In various configurations, the virus can be an AAV2 and the second ammonium sulfate concentration can be from 35% to 40% saturation. In various configurations, the virus can be an AAV5 and the second ammonium sulfate concentration can be from 35% to 40% saturation. In various configurations, the virus can be AAV6 and the second ammonium sulfate concentration can be from 30% to 35% saturation. In various configurations, the separating the second mixture can comprise settling the second mixture for about 30 to about 60 minutes. In various configurations, the separating the second mixture can comprise centrifuging the second mixture. In some configurations, the centrifuging the second mixture can comprise centrifuging the second mixture at about 4000 rpm (about 4293×g) for about 10 min. In various configurations, a method of the present teachings can further comprise subjecting the second aqueous phase collected in h) to a cesium chloride density gradient purification procedure.

In various configurations, a method of the present teachings can further comprise subjecting the first aqueous phase collected in d) to a column chromatography purification procedure. In some configurations, the column chromatography purification procedure can be selected from the group consisting of heparin affinity chromatography, HPLC heparin affinity chromatography, and HPLC cation exchange chromatography. (Zolotukhin, S., et al., Gene Therapy 6, 973-985, 1999.) In some configurations, the column chromatography purification procedure is selected from the group consisting of an ion-exchange chromatography procedure, a gel filtration chromatography procedure, and a combination thereof. (Tomono, T., et al., Molecular Therapy—Methods & Clinical Development 3, 15058, 2016.) In various configurations, a method of the present teachings can further comprise subjecting the first aqueous phase collected in d) to a density gradient purification centrifugation procedure.

In various configurations, a method of the present teachings can further comprise subjecting the first aqueous phase collected in d) to a sucrose density gradient purification procedure.

In various configurations, a method of the present teachings can further comprise subjecting the first aqueous phase collected in d) to a cesium chloride density gradient purification procedure.

In various configurations, a method of the present teachings can further comprise subjecting the first aqueous phase collected in d) to an iodixanol density gradient purification procedure.

In various configurations, in a method of the present teachings, the cell lysate comprising a virus can be a lysate of an insect cell comprising a virus. In some configurations, the insect cell comprising a virus can be an Sf9 cell comprising a virus.

In various configurations, the insect cell comprising a virus can be an Sf9 cell comprising an AAV.

In various configurations, in a method of the present teachings, the cell lysate comprising a virus is a lysate of a mammalian cell comprising a virus. In some configurations, the mammalian cell comprising a virus can be an HEK293 cell comprising a virus. In some configurations, the mammalian cell comprising a virus can be an HEK293 cell comprising an AAV.

In various embodiments, a composition of the present teachings can comprise a cell lysate comprising a virus; ammonium sulfate; and t-butanol. In some configurations, the ammonium sulfate can be at a concentration in which t-butanol is immiscible with water. In various configurations, the virus can be a non-enveloped virus. In various configurations, the virus can be selected from the group consisting of an adenovirus and an adeno-associated virus. In various configurations, the virus can be an adeno-associated virus. In various configurations, the virus can be selected from the group consisting of an AAV2, an AAV5 and an AAV6. In various configurations, the cell lysate comprising a virus can be a cell lysate of an insect cell comprising a virus. In various configurations, the cell lysate comprising a virus can be a cell lysate of an Sf9 insect cell comprising an adeno-associated virus. In various configurations, the cell lysate comprising a virus can be a cell lysate of an Sf9 insect cell comprising an adeno-associated virus selected from the group consisting of an AAV2, an AAV5 and an AAV6.

In various embodiments, the present teachings can encompass an AAV virus purified by the method as disclosed herein.

DETAILED DESCRIPTION

Figure 1:
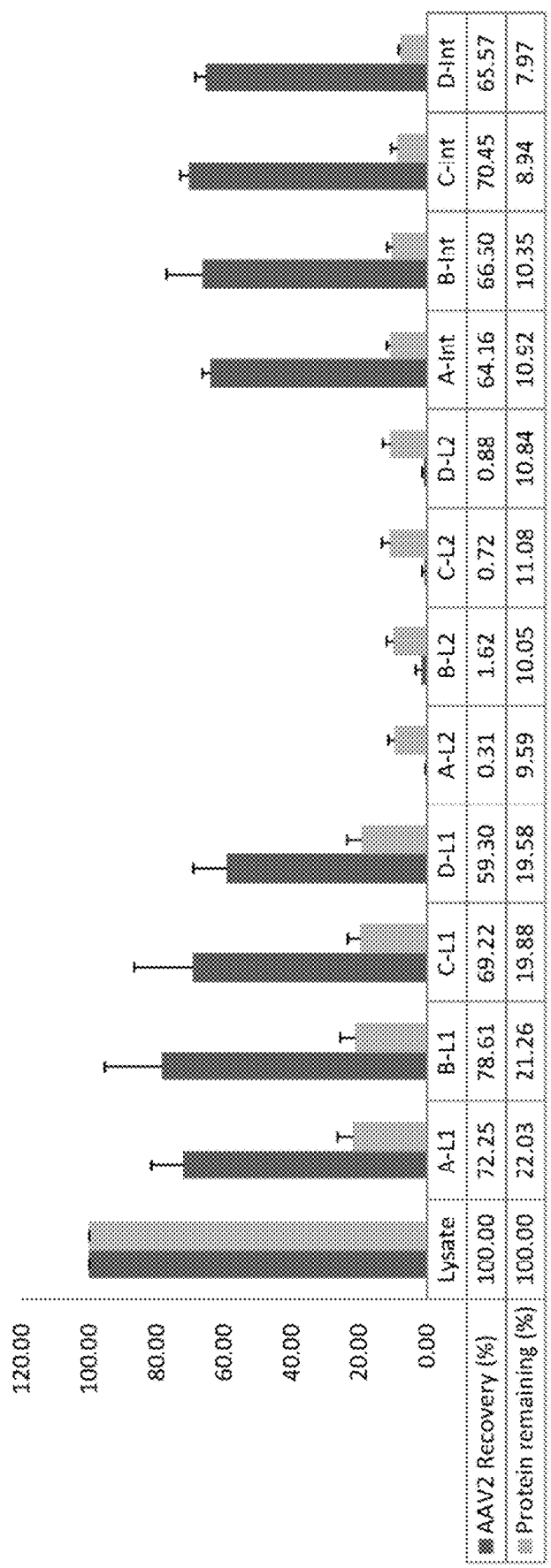
FIG. 1 illustrates the effects of different ammonium sulfate saturations in the first round of TPP on AAV2 recovery.

The inventor has developed methods of purifying a virus from a cell lysate, such as, for example, an adeno-associated virus from an insect cell lysate, using three-phase partitioning.

In various configurations, a method of the present teachings can comprise a first round of three phase partitioning (TPP), i.e., a) forming a first (or only) composition comprising i) a cell lysate comprising a virus, ii) ammonium sulfate, and iii) t-butanol; b) agitating the first (or only) composition, e.g., by shaking or vortexing, thereby forming a first (or only) mixture, c) separating the first (or only) mixture into a first (or only) aqueous phase, a first (or only) interphase and a first (or only) organic phase (i.e., forming layers comprising an aqueous phase, an interphase, and an organic phase); and d) collecting the first (or only) aqueous phase. In various configurations, the ammonium sulfate can be at a first (or only) concentration in which t-butanol is immiscible with water. In various configurations, methods of the present teachings can further comprise a second round of TPP, which can comprise e) forming a second composition comprising i) a first aqueous phase collected in d), ii) ammonium sulfate at a second concentration in which t-butanol is immiscible with water, and iii) t-butanol. In various configurations, the second composition can be agitated, thereby forming a second mixture. In various aspects, after the agitating, the second mixture can be separated into at least three phases, including a second organic phase, a second interphase, and a second aqueous phase. In various aspects, the second interphase, which can comprise the majority of the virus, can be collected. In various configurations, the aqueous phase can comprise the virus with reduced impurities such as cell debris and cell protein compared to the lysate.

In various configurations, the virus can be any virus that can be grown in vitro, or any non-enveloped virus that can be grown in vitro. Non-limiting examples of a non-enveloped virus include a virus from the families Picornaviridae (e.g. Enterovirus, rhinovirus, hepatovirus, cardiovirus, aphthovirus, poliovirus, parechovirus, erbovirus, kobuvirus, teschovirus, or coxsackie virus), Parvoviridae (e.g., Parvovirus B19, canine parvovirus, or human bocavirus), Anelloviridae (e.g. Torque teno virus), Papovaviridae (e.g., Papillomavirus, polyomaviridae, simian vacuolating virus), Adenoviridae (e.g., Adenovirus, Adeno-associated virus, Infectious canine hepatitis virus), Reoviridae (e.g., Reovirus, rotavirus), Caliciviridae (e.g., Norwalk virus, Calicivirus), Astroviridae (e.g., Astrovirus), Caulimoviridae (e.g., cauliflower mosaic virus), Circoviridae, Birnaviridae, or Potyviridae, (potyvirus barley yellow mosaic virus). In some configurations, a virus that can be isolated by a method of the present teachings can be an adenovirus or an adeno-associated virus (AAV), such as, for example and without limitation, an AAV2, an AAV5 or an AAV6.

In various configurations, a cell lysate can be a cell lysate of virus-infected insect cells such as, without limitation, Sf9 cells infected with an AAV, or virus-infected mammalian cells such as, without limitation, AAV-infected HEK293 cells. In various configurations, in a TPP procedure of the present teachings, ammonium sulfate can be added to a sample comprising a virus, followed by addition of t-butanol.

In general, a method of TPP purification requires saturation of a salt such that t-butanol is no longer miscible in water so that the aqueous and organic solvents can separate into phases. Ammonium sulfate is a suitable salt, and generally the required concentrations to render t-butanol immiscible are 10 to 40% saturation of ammonium sulfate. As disclosed herein, a method of the present teachings can be optimized for a particular virus. For example, recovery of AAV2 is optimal when the first (or only) ammonium sulfate concentration is from 10% to 25% saturation and the second ammonium sulfate concentration (if performed) is from 35% to 40% saturation. Recovery of AAV5 is optimal when the first (or only) ammonium sulfate concentration is from 10% to 20% saturation and the second ammonium sulfate concentration (if performed) is from 35% to 40% saturation. Recovery of AAV6 is optimal when the first (or only) ammonium sulfate concentration is from 15% to 30% saturation and the second ammonium sulfate concentration (if performed) is from 30% to 35% saturation. Skilled artisans will be able to optimize the methods of the present teachings to other viruses based on the examples herein using routine experimentation.

Also disclosed are experiments to optimize lysate pH for viral recovery. Optimal viral recovery occurs at pH 6.5 for AAV2 and AAV5 with diminishing returns on further lowering pH. In general, optimal recovery occurs at a pH of 5.5 to 7.5, and a skilled artisan would be able to optimize pH for additional viruses using routine experimentation.

In various configurations, viruses purified by a method of the present teachings-including one purification or two purifications—can be further purified by additional purification methods previously known in the art such as, without limitation, a column chromatography procedure, such as heparin affinity chromatography, HPLC heparin affinity chromatography, or HPLC cation exchange chromatography. Column chromatography procedures known in the art suitable for use in methods of the present teachings include ion-exchange chromatography, gel filtration chromatography procedure. Ion-exchange chromatography can include desalting columns and ion-exchange membranes. Such methods are known in the art.

Methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Nagy, A., Manipulating the Mouse Embryo: A Laboratory Manual (Third Edition), Cold Spring Harbor, N.Y., 2003 and Harlow, E., Using Antibodies: A Laboratory Manual, Cold Spring Harbor Laboratory Press, Cold Spring Harbor, N.Y., 1999. As used in the present description and any appended claims, the singular forms "a", "an" and "the" are intended to include the plural forms as well, unless the context indicates otherwise.

All centrifuge speeds are given in both rpm and x g. Skilled artisans will recognize that these conversions will depend on the rotor used, and that forces expressed in x g will be constant, regardless of the actual RPM of the rotor.

Materials and Methods

Sf9 cell culture. Sf9 cells (Jeang, K. T., et al., J. Virol. 61: 708-713, 1987) were cultured in CORNING® (Corning, Inc., Tewksbury, Mass.) storage bottles at 28° C. in ESF 921™ medium (Expression Systems, Davis, Calif.) supplemented with 100 units/ml penicillin and 100 g/ml streptomycin (Mediatech, Inc., Manassas, Va.). The cells were split 1:4 once the cell density reached $1.00 \times 10^7$ cells/ml for maintenance.

HEK293 cell culture. Human embryo renal cortical (HEK293) cells (Simmons, N. L., Experimental Physiol. 75, 309-319, 1990) were cultured in T-75 flasks in DMEM media supplemented with 100 units/ml penicillin and 100 µg/ml streptomycin (Mediatech) and 10% FBS (ATCC, Manassas, Va.). The flasks were incubated at 37° C. in a $CO_2$ incubator. The cells were split 1:10 once they reached confluence for maintenance purposes.

Production of AAV particles. AAV particle production was performed according to Virovek standard protocols (Chen, H., Methods Mol. Biol. 2011; 737:235-46). Briefly, Sf9 cells were cultured to about $1.00 \times 10^7$ cells/ml and diluted 1:1 with fresh ESF™ 921 media. 10 moi of recombinant baculovirus (rBV) containing the designated rep-cap genes and 5 moi of rBV containing a gene of interest (such as, for example, a gene encoding a green fluorescent protein or a luciferase) were added to infect the Sf9 cells for 3 days at 28° C. in a shaker incubator. The infected Sf9 cells were harvested by centrifugation at 2415×g for 10 min and stored at −20° C. before use.

Preparation of cell lysate. Cell pellets containing AAV particles were lysed in Sf9 lysis buffer (50 mM Tris-HCl, pH 7.8, 500 mM NaCl, 2 mM $MgCl_2$, 1% Sarkosyl, and 1% TRITON™ X-100 (Dow Chemical Company, Midland, Mich.)), and 60 units/ml ARCTICZYMES® HL-SAN non-specific endonuclease (ArcticZymes, Inc., Plymouth Meeting, Pa.) by sonicating for 30 seconds. Genomic DNA was digested by incubation at 37° C. for one hour.

Three phase partitioning. Ammonium sulfate powder was added to the cell lysate at the saturations discussed infra and dissolved by vortexing. An equal volume of t-butanol was added to the cell lysate and mixed through vigorous shaking for 1 min. The cell lysate-t-butanol mixture was centrifuged at 4293×g for 10 min to form three phases. After removing the upper phase, the lower aqueous phase (L1) containing AAV particles was collected and the interphase, which contained the majority of cellular proteins and other cellular debris, was discarded. This completed the first round of TPP. The aqueous (L1) phase now can be used for column chromatography, density gradient centrifugation processes, or a second round of TPP to further purify AAV vectors.

For a second round of TPP, the saturation level of ammonium sulfate in L1 was brought up to the desired saturation as necessary. An equal amount of t-butanol was then added and mixed with vigorous shaking for 1 min. The aqueous-t-butanol mixture was centrifuged at 4293×g for 10 min to form three phases. The upper and lower phases were both removed, and the interphase containing AAV particles was dissolved by sonication for 1 min in the Sf9 lysis buffer containing 100 mM sodium citrate (50 mM Tris-HCl, pH 7.8, 500 mM NaCl, 2 mM $MgCl_2$, 100 mM sodium citrate, 1% Sarkosyl, and 1% TRITON™ X-100) followed by rocking at room temperature for 1 hour. The dissolved interphase was then centrifuged at 10322×g for 20 min to remove insoluble debris. The supernatant was used for buffer exchange and sterile filtration. The amount of AAV particles was determined using a quantitative PCR (QPCR) assay, and purity was determined by SDS-PAGE and staining.

Column chromatography purification of AAV-Samples containing AAV particles in the aqueous L1 can be further purified using MUSTANG® S and MUSTANG® Q membrane coins (Pall Industries, Port Washington, N.Y.) according to Manufacturer's protocol. Briefly, the MUSTANG® S and Q coins can be first treated with 10 mL of 1M NaOH followed by 10 mL of 1M NaCl and 10 mL of 20 mM Tris-HCl (pH 9.0). Then 5 mL of L1 AAV sample desalted with PD-10 desalting columns can be diluted 1:10 with 20 mM Tris-HCl (pH9.0) and applied to the Mustang S coin. The flow-through can be collected and applied to the MUSTANG® Q coin. After washing with 1.5 mL of 20 mM Tris-HCl (pH 9.0), the AAV particles can be eluted with elution buffer (20 mM Tris-HCl (pH 9.0), 300 mM NaCl), desalted with PD-10 desalting columns, and titers can be determined with a QPCR method.

Density gradient purification of AAV-Samples containing AAV particles in the aqueous L1 can be loaded onto the top of step gradient with 1.55 g/cc and 1.32 g/cc of CsCl solutions and centrifuged at 28,000 rpm overnight (~20 hours). AAV particles can be collected with a syringe, desalted with PD-10 desalting columns and titers can be determined with a qPCR method.

SDS-PAGE and protein staining. Samples containing AAV particles were mixed with SDS-PAGE loading buffer (Invitrogen) and heated at 95° C. for 5 min. They were then loaded onto a 10% SDS-PAGE gel and run at 100 V until the dye (Bromophenol Blue) reached the bottom of the gel. The gel was stained according to the manufacturer's protocol (Invitrogen).

Measurement of protein concentration. Protein concentrations in cell lysates were measured using a PIERCE™ BCA Protein Assay Kit (Pierce Biotechnology, Rockford, Ill.) according to manufacturer's protocol. Briefly, 25 µL of samples containing AAV particles were each mixed with 200 µL of PIERCE™ BCA Protein Assay Reagent mixture (50 parts Reagent A mixed with 1 part Reagent B). After incubation at room temperature for 15-20 min, the OD values were recorded in the Tecan ULTRA 384 plate reader (Morrisville, N.C.).

Quantification of AAV particles. The quantities of AAV particles were determined using a quantitative real-time PCR assay using a CHROMO4™ system (Bio-Rad Laboratories, Inc., Hercules, Calif.) in accordance with the manufacturer's protocol. Briefly, AAV samples were digested with DNaseI for one hour at 37° C. to remove contaminating DNA from the surface of the virus particles. At the end of digestion, the AAV samples were mixed with an equal volume of 200 mM EDTA and heated to 95° C. for 30 min to inactivate the DNaseI. The digested AAV samples were then analyzed by a QPCR assay in the CHROMO4™ Real-Time Detector.

Assay of AAV infectivity. Purified AAV particles are used to transduce HEK293 cells to determine the particles' infectivity. Briefly, AAV particles are diluted in DMEM containing 20 µM etoposide and added to the HEK293 cells in 24-well plates. After incubation at 37° C. in a $CO_2$ incubator for 3 days, GFP-expressing cells can be photographed, analyzed and compared with AAV particles purified using a conventional CsCl ultracentrifugation method.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates the effects of varying ammonium sulfate saturation levels on AAV2 distribution in the first round of TPP of cell lysates subjected to TPP.

Initially, it was found that subjecting cell lysates to a first round of TPP resulted in AAV2 particles remaining in the aqueous phase while cellular proteins and cell debris formed a solid interphase. A second round of TPP led to the AAV particles forming a solid interphase, with cellular proteins and cell debris remaining in the aqueous phase. In further experiments, the effects of varying ammonium sulfate saturation values in the first round of TPP on AAV2 distribution on cell lysates subjected to TPP were investigated. The results, displayed in FIG. 1, are representative of averages of lysates from three independent experiments. In FIGS. 1, A, B, C, and D correspond to cell lysates from AAV2-infected Sf9 cells with 10%, 15%, 20%, and 25% saturation of ammonium sulfate, respectively in the first round of TPP; L1 represents the aqueous phase after the first round of TPP; L2 represents the aqueous phase after the second round of TPP at fixed 35% saturation of ammonium sulfate; Int represents the interphase after the second round of TPP at fixed 35% saturation of ammonium sulfate. Error bars indicate standard deviation.

Maximum distribution of AAV2 to the aqueous phase in the first round was achieved at 15% ammonium sulfate saturation. When the saturation value of ammonium sulfate in the first round of TPP was increased to 25%, there was a slight decrease of AAV2 in the aqueous phase (FIG. 1, compare D-L1 with C-L1 and D-Int with C-Int). In the second round, maximum distribution of AAV2 to the interphase was observed from lysates subjected to 20% saturation of ammonium sulfate in the first round (C-Int).

Protein assays were performed to monitor the removal of cellular proteins through the whole TPP process. The results presented in FIG. 1 indicate that from 70% to 80% of cellular proteins were removed in the first round of TPP. Furthermore, there is a slight increase of protein-removal power with the increase of saturation value of ammonium sulfate from 10% to 30%.

Example 2

This example illustrates the effects on AAV5 distribution of varying ammonium sulfate saturation levels in the first round of TPP of cell lysates subjected to TPP.

Figure 2:
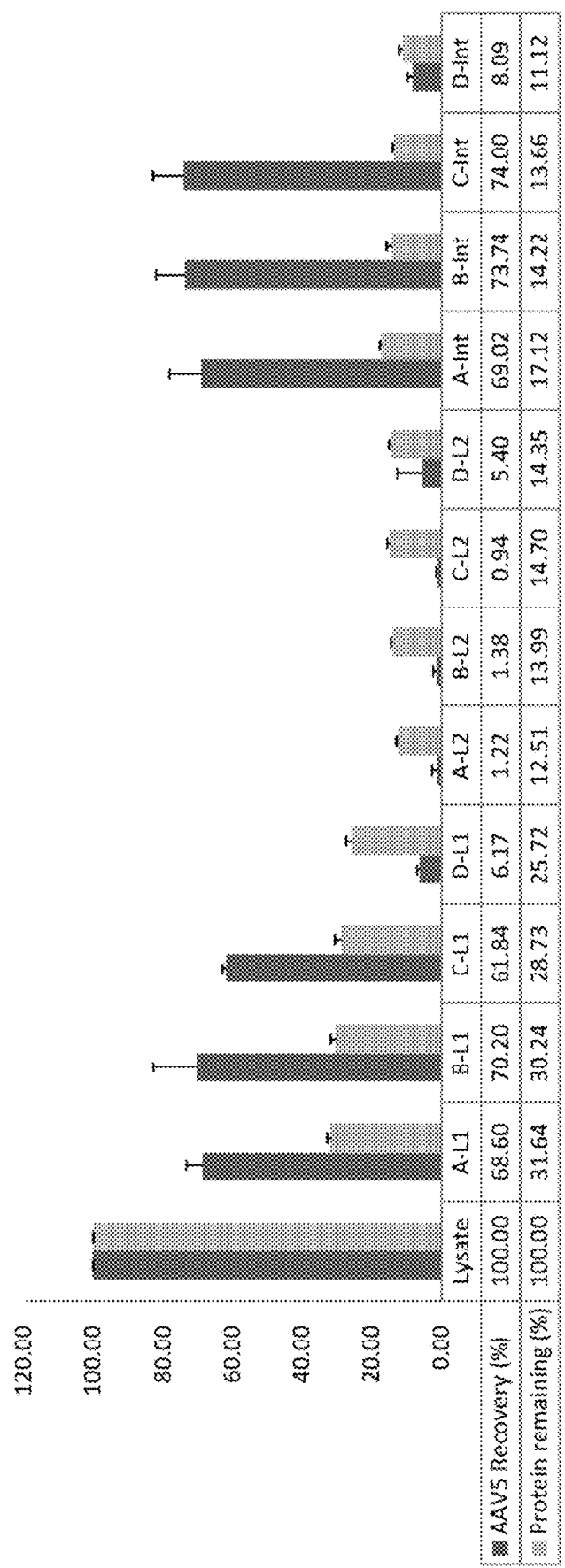
FIG. 2 illustrates the effects of different ammonium sulfate saturations in the first round of TPP on AAV5 recovery.

In these experiments, the effects of varying ammonium sulfate saturation values in the first round of TPP on AAV5 distribution on cell lysates subjected to TPP were investigated. The results, displayed in FIG. 2, are representative of average values from three lysates with 10%, 15%, 20%, and 25% saturation of ammonium sulfate (A, B, C and D, respectively) in the first round of TPP; L1 represents the aqueous phase after the first round of TPP; L2 represents the aqueous phase after the second round of TPP at a fixed 35% saturation of ammonium sulfate; Int represents the interphase after second round of TPP at fixed 35% saturation of ammonium sulfate.

When cell lysates containing AAV5 vectors were subjected to a first round of TPP with 10%, 15%, 20%, or 25% ammonium sulfate saturation, and a second round of TPP with fixed 35% saturation of ammonium sulfate, a major decrease of AAV5 vectors in the aqueous phase was observed at 25% ammonium sulfate saturation (FIG. 2, compare D-L1 with C-L1 and D-Int with C-Int). Protein assays indicate that the majority of cellular proteins (from 69% to 62%) were removed in the first round of TPP. The second round of TPP removed additional cellular proteins. Only 17% or less of cellular proteins remained in the interphase containing the AAV5 vectors.

Protein assays were performed to monitor the removal of cellular proteins through the whole TPP process. The results from FIG. 2 indicate that from 70% to 80% of cellular proteins were removed in the first round of TPP. There is a slight increase of protein-removal power with the increase of saturation value of ammonium sulfate from 10% to 30%.

Example 3

This example illustrates the effects on AAV6 distribution of varying ammonium sulfate saturation levels in the first round of TPP of cell lysates subjected to TPP.

Figure 3:
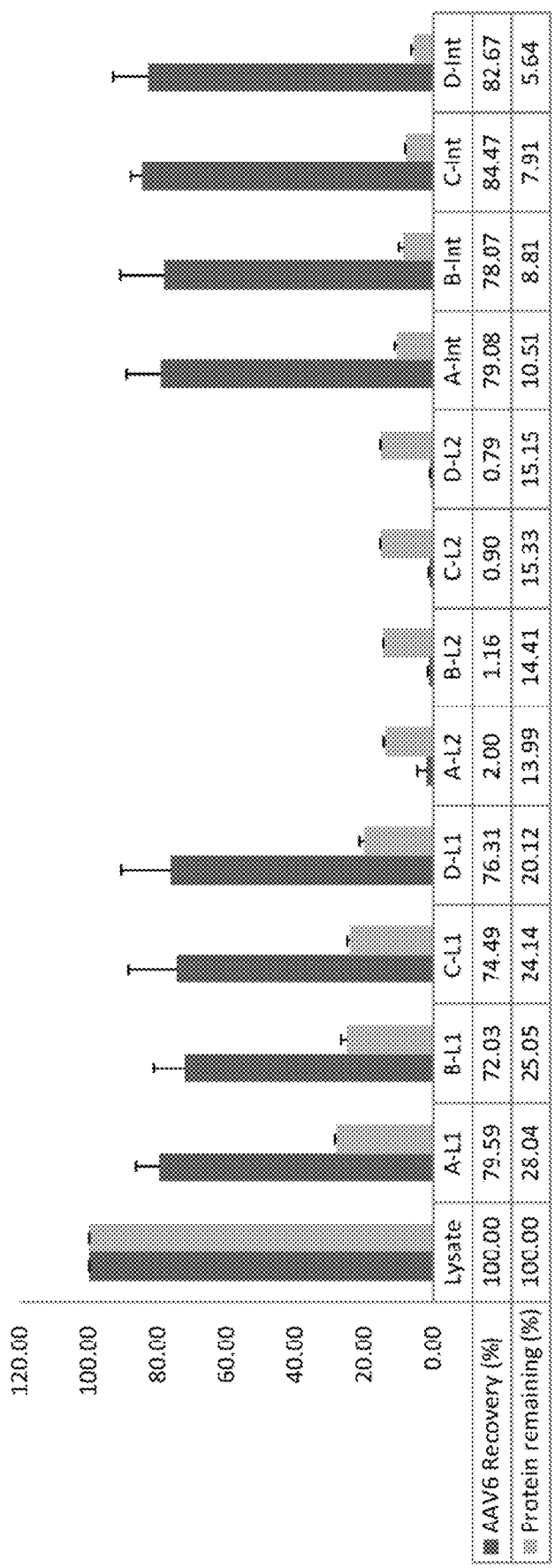
FIG. 3 illustrates the effects of different ammonium sulfate saturations in the first round of TPP on AAV6 recovery.

In these experiments, the effects of varying ammonium sulfate saturation levels in the first round of TPP on AAV6 distribution on cell lysates subjected to TPP were investigated. The results, displayed in FIG. 3, are representative of average values from three lysates. A, B, C, and D represent cell lysates with 15%, 20%/a, 25%, and 30% ammonium sulfate saturation levels, respectively in the first round of TPP; L1 represents the aqueous phase after the first round of TPP; L2 represents the aqueous phase after the second round of TPP at a fixed concentration of 35% saturation of ammonium sulfate; Int represents the interphase after the second round of TPP at a fixed concentration of 35% saturation of ammonium sulfate.

When cell lysates containing AAV6 vectors were subjected to the first round of TPP with 15%, 20%, 25%, or 30% saturation of ammonium sulfate, and the second round of TPP with fixed 35% saturation value of ammonium sulfate, AAV6 recovery was steady across the treatments, even when the ammonium sulfate saturation was increased to 30% in the first round. This differs from AAV2, which showed a slight decrease at 25% ammonium sulfate, and from AAV5, which did not benefit from increased ammonium sulfate beyond 20% saturation.

Protein assays were performed to monitor the removal of cellular proteins through the whole TPP process. The results presented in FIG. 3 indicate that from 70% to 80% of cellular proteins were removed in the first round of TPP. There is a slight increase of protein-removal power with the increase of saturation value of ammonium sulfate from 10% to 30%.

Example 4

This example illustrates the effects on AAV2 distribution of varying ammonium sulfate saturation levels in the second round of TPP on cell lysates subjected to TPP.

Figure 4:
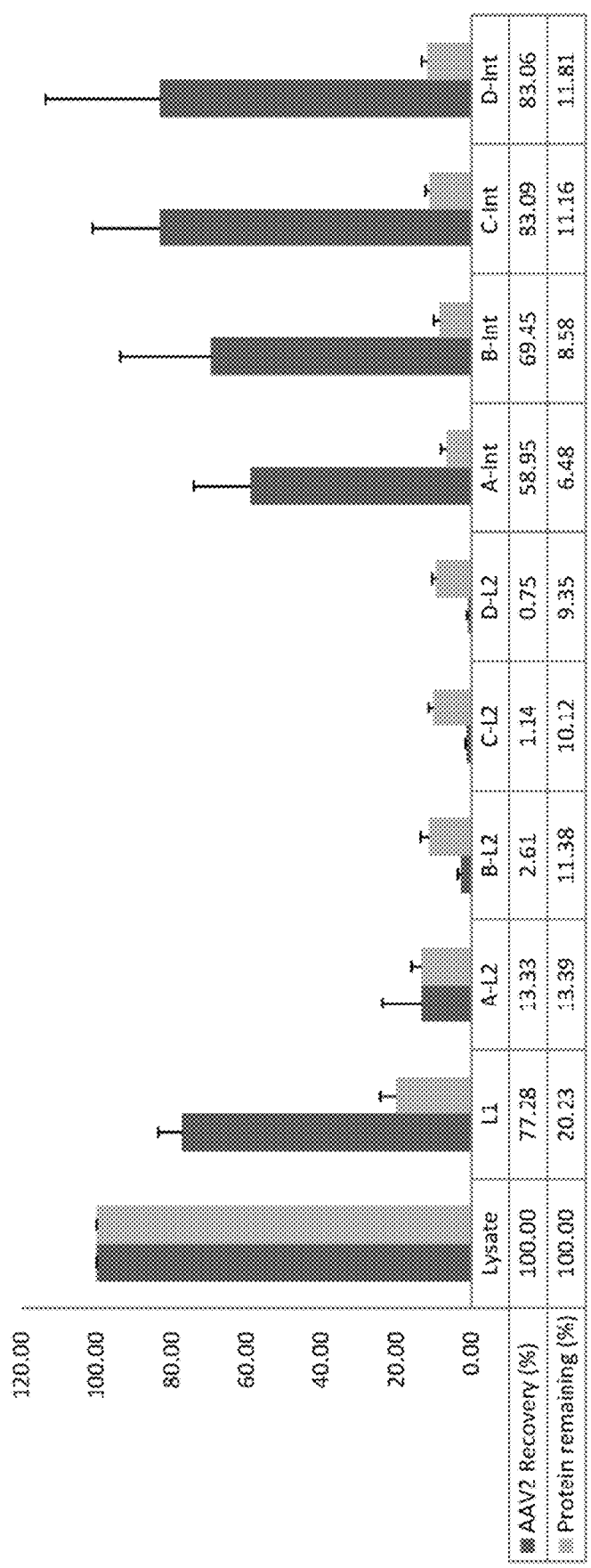
FIG. 4 illustrates the effects of different ammonium sulfate saturations in the second round of TPP on AAV2 recovery.

In these experiments, cell lysates containing AAV2 vectors were subjected to a first round of TPP with a fixed 20% saturation of ammonium sulfate. The aqueous phase for each AAV2 sample was then divided to 4 fractions, and each fraction was then subjected to a second round of TPP with 25%, 30%, 35%, or 40% saturation of ammonium sulfate. The aqueous phase and interphase were collected and the AAV2 titer determined. The results are shown in FIG. 4. FIG. 4 illustrates results from three independent experiments: L1 represents the aqueous phase after the first round of TPP at a fixed 20% saturation of ammonium sulfate; A, B, C, and D represent the aqueous phase L1 divided into 4 fractions and adjusted to contain 25%, 30%, 35%, or 40% saturation of ammonium sulfate respectively in the second round of TPP; L2 represents the aqueous phase after the second round of TPP; Int represents the interphase after the second round of TPP. Substantial AAV recovery was observed for all saturation values tested. Among the 4 different saturation values tested, 35% saturation showed the highest recovery rate for all three AAV1 samples in the interphase (see FIG. 4, Int).

Example 5

Figure 5:
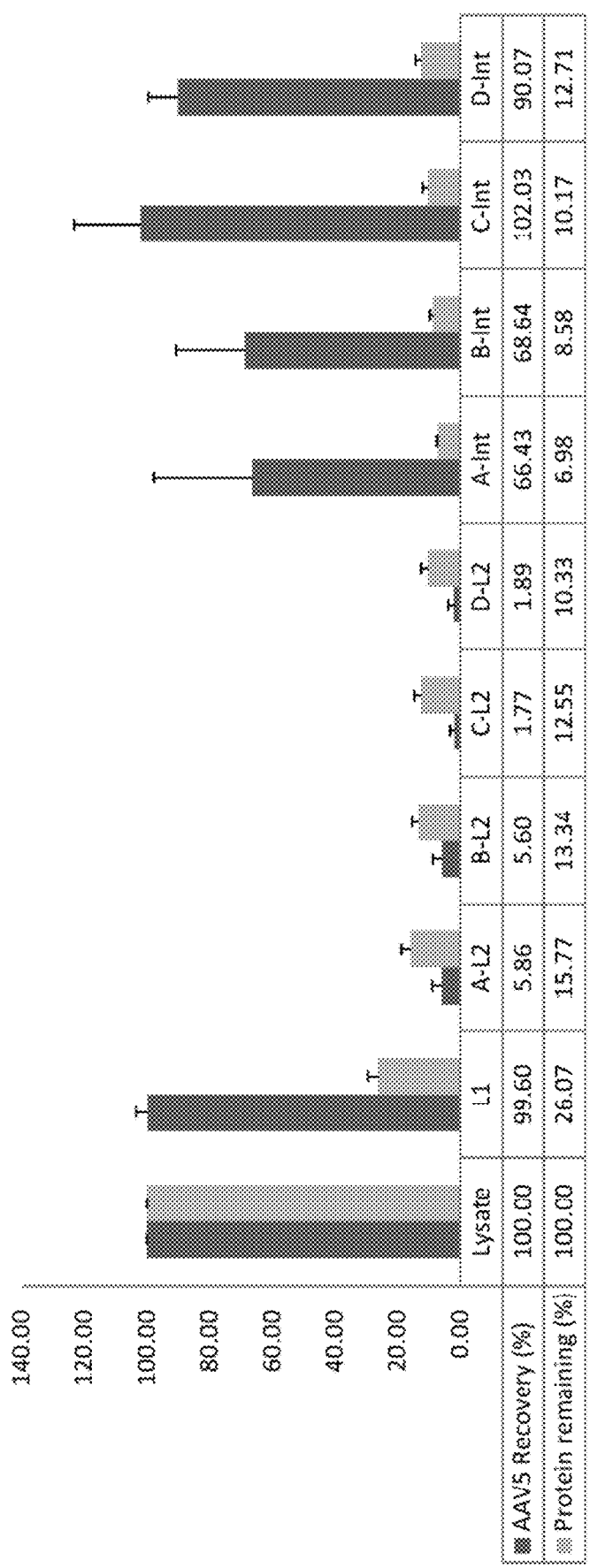
FIG. 5 illustrates the effects of different ammonium sulfate saturations in the second round of TPP on AAV5 recovery.

This example illustrates the effects on AAV5 distribution of varying ammonium sulfate saturation levels in the second round of TPP of cell lysates subjected to TPP. In these experiments, cell lysates containing AAV5 vectors were subjected to a first round of TPP with a fixed 20% saturation of ammonium sulfate. The aqueous phase for each AAV5 sample was then divided to 4 fractions, and each fraction was subjected to a second round of TPP with 25%, 30%, 35%, or 40% saturation of ammonium sulfate. Each aqueous phase and interphase was collected and the AAV5 titer determined. The results are shown in FIG. 5. FIG. 5 illustrates results from three independent experiments: L1 represents the aqueous phase after the first round of TPP at a fixed 20% saturation of ammonium sulfate; A, B, C, and D represent the aqueous phase L1 divided into 4 fractions and adjusted to contain 25%, 30%, 35%, or 40% saturation of ammonium sulfate respectively in the second round of TPP; L2 represents the aqueous phase after the second round of TPP; Int represents the interphase after the second round of TPP. Substantial AAV recovery was observed for all saturation values tested. Among the 4 different saturation values tested, 35% saturation showed the highest recovery rate for AAV5 samples in the interphase (see FIG. 5, Int).

Example 6

This example illustrates the effects on AAV6 distribution of varying ammonium sulfate saturation levels in the second round of TPP of cell lysates subjected to TPP.

Figure 6:
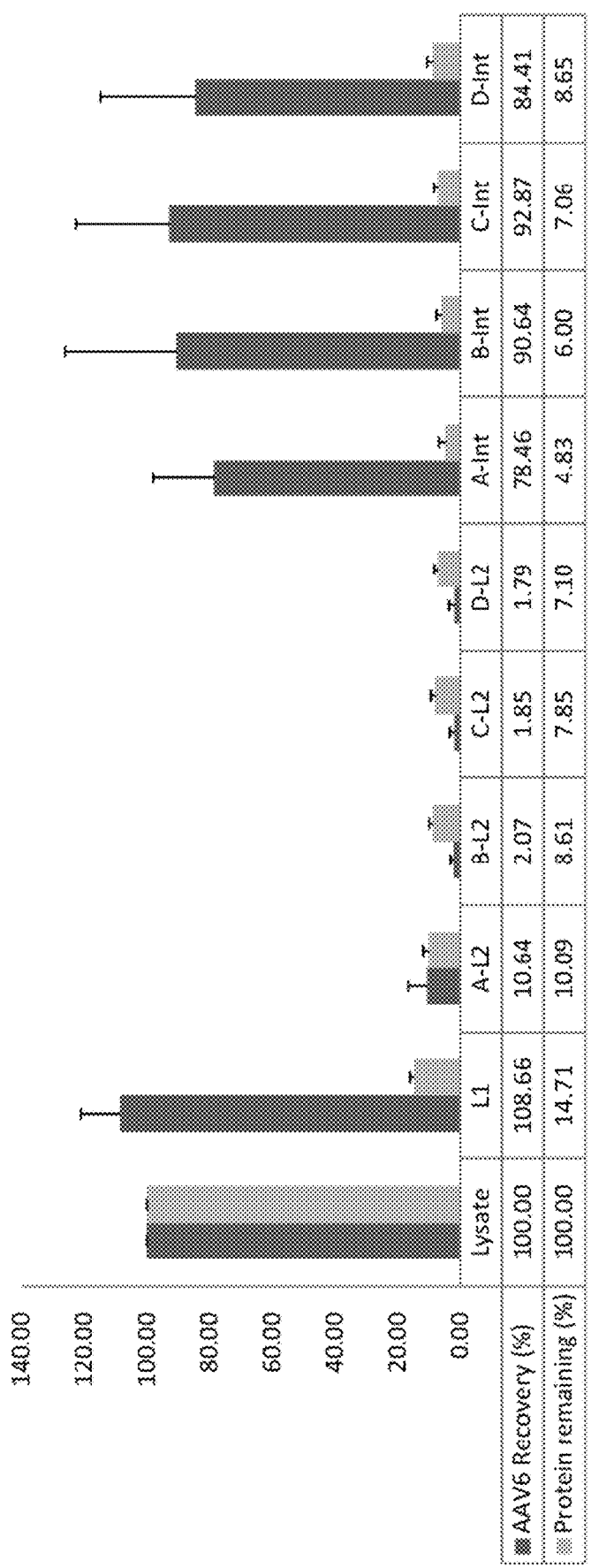
FIG. 6 illustrates the effects of different ammonium sulfate saturations in the second round of TPP on AAV6 recovery.

In these experiments, cell lysates containing AAV6 vectors were subjected to a first round of TPP with a fixed 20% saturation of ammonium sulfate. The aqueous phase for each AAV5 sample was divided to 4 fractions; each fraction was subjected to a second round of TPP with 25%, 30%, 35%, or 40% saturation of ammonium sulfate. The aqueous phase and interphase were collected and the AAV5 titer determined. The results are shown in FIG. 6. FIG. 6 illustrates results from three independent experiments: L1 represents the aqueous phase after the first round of TPP at a fixed 20% saturation of ammonium sulfate; A, B, C, and D represent the aqueous phase L1 divided into 4 fractions and adjusted to contain 25%, 30%, 35%, or 40% saturation of ammonium sulfate respectively in the second round of TPP; L2 represents the aqueous phase after the second round of TPP; Int represents the interphase after the second round of TPP. Substantial AAV recovery was observed for all saturation values tested. Among the 4 different saturation values tested, 35% saturation showed the highest recovery rate for AAV6 samples in the interphase (see FIG. 6, Int).

Example 7

This example illustrates the effects of altering pH on AAV2 distribution in cell lysates subjected to TPP.

Figure 7:
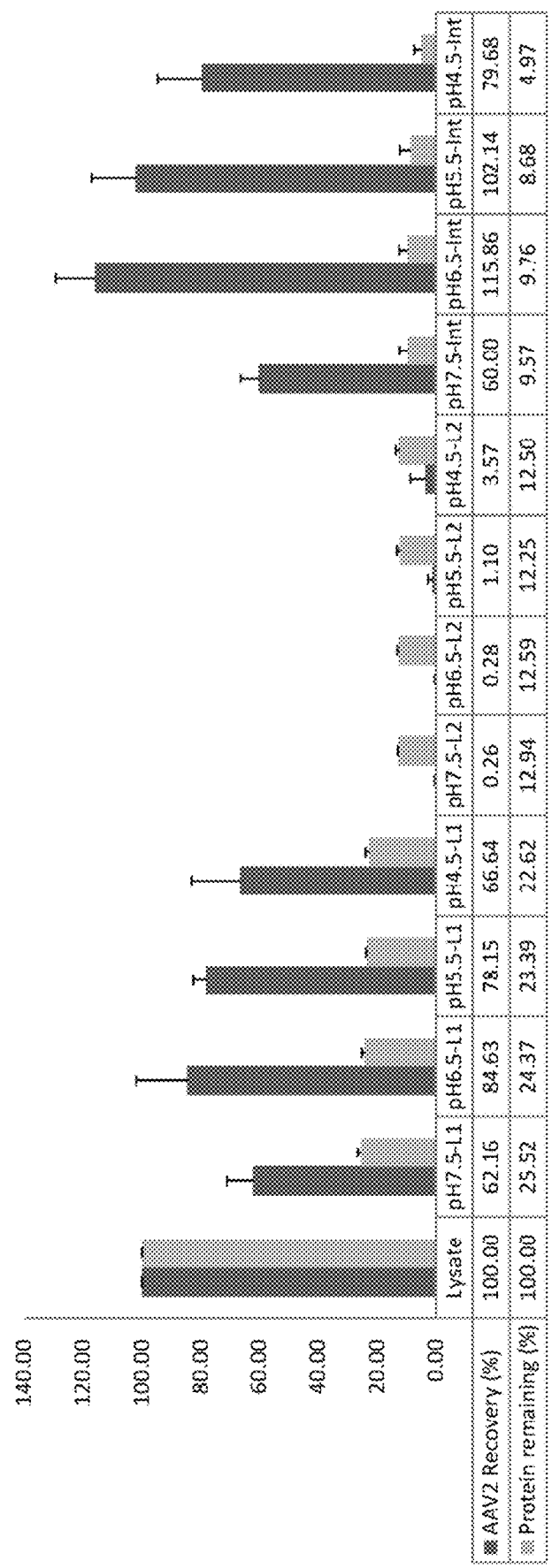
FIG. 7 illustrates the effects of different pH values on AAV2 vector recovery in a TPP method of the present teachings.

In these experiments, the pH conditions were varied in cell lysates for AAV2 purification using TPP. Cell lysates containing AAV2 vectors were prepared in Sf9 lysis buffer (pH 7.5) at 20% ammonium sulfate saturation and then divided into 4 fractions. After incubation with nuclease for 1 hour at 37° C. to digest the cellular nucleic acids, ammonium sulfate was added to 20% saturation and the lysate was divided into 4 equal fractions. Three fractions of the lysate were adjusted to pH 6.5, pH 5.5, and pH 4.5 respectively with acetic acid; the fourth fraction was used to test the lysate at pH 7.5. All the lysates were then subjected to two rounds of TPP, and the AAV2 titers were then determined. The results are shown in FIG. 7. In FIG. 7, L1 represents the aqueous phase after a first round of TPP at fixed 20% ammonium sulfate saturation; L2 represents the aqueous phase after second round of TPP at fixed 35% ammonium sulfate saturation; Int represents the interphase after a second round of TPP.

The majority of AAV2 vectors were recovered in the interphase in all pH values tested, but pH 6.5 showed the greatest AAV2 recovery rate (FIG. 7, pH 6.5-Int).

Protein assays were performed to monitor the cellular protein removal at different pH values. The results indicate that as pH values decreased, more cellular proteins were removed. More than 95% cellular proteins were removed from the AAV2 samples when the cell lysates were adjusted to pH 4.5 (FIG. 7, pH 4.5-Int).

Example 8

This example illustrates the effects of varying pH on AAV5 distribution on cell subjected to TPP.

Figure 8:
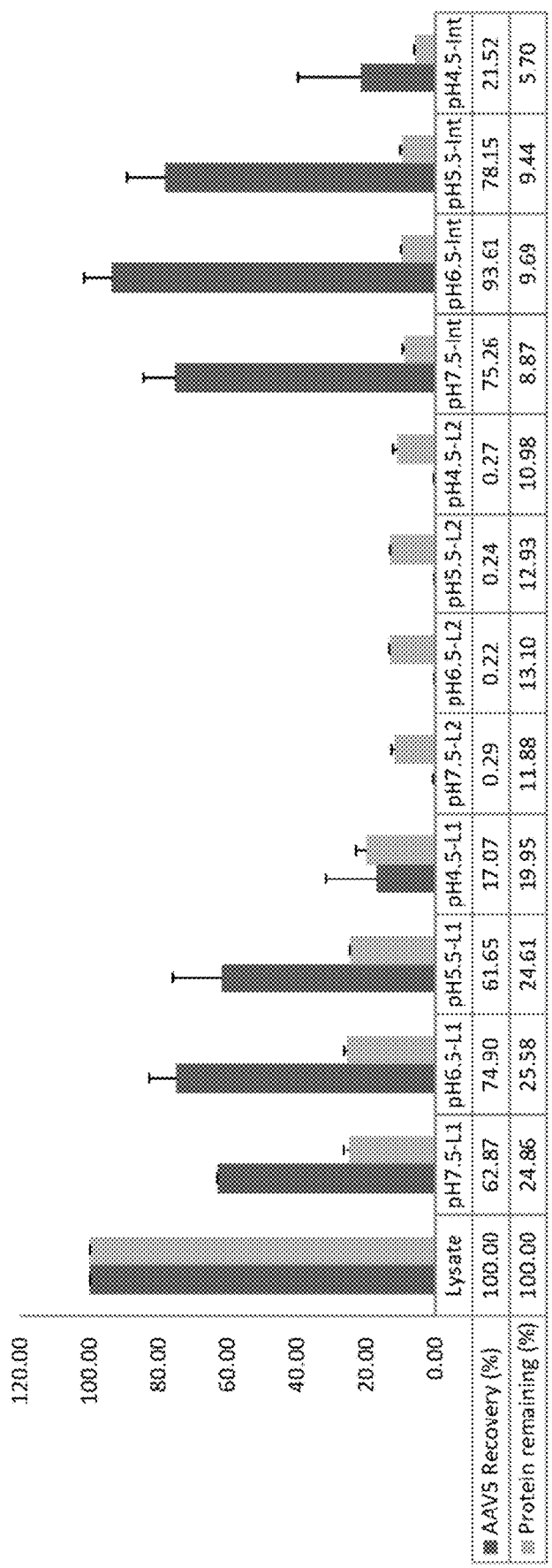
FIG. 8 illustrates the effects of different pH values on AAV5 vector recovery in a TPP method of the present teachings.

In these experiments, the pH conditions were varied in cell lysates for AAV5 purification in TPP. Cell lysates containing AAV5 vectors were prepared in Sf9 lysis buffer (pH 7.5) at 20% ammonium sulfate saturation and then divided into 4 fractions. After incubation with nuclease for 1 hour at 37° C. to digest the cellular nucleic acids, ammonium sulfate was added to 20% saturation; the lysates were then divided into 4 equal parts. Three fractions were adjusted to pH 6.5, pH 5.5, and pH 4.5 respectively with acetic acid, the fourth fraction was used to test the lysate at pH 7.5. All the lysates were then subjected to two rounds of TPP; the AAV5 titers were then determined. The results are shown in FIG. 8. In FIG. 8, L1 represents the aqueous phase after the first round of TPP at fixed 20% saturation of ammonium sulfate; L2 represents the aqueous phase after second round of TPP at fixed 35% saturation of ammonium sulfate; Int represents the interphase after a second round of TPP.

The majority of AAV5 vectors were recovered from pH 7.6, pH 6.5, and pH 5.5. However, nearly 80% of AAV5 vectors were lost when the pH value of the lysate decreased to 4.5 (FIG. 8, pH 4.5-Int).

Protein assays were performed to monitor the cellular protein removal at different pH values. The results indicate that as pH values decreased, more cellular proteins were removed. However, the removal of cellular proteins resulted in a significant loss of AAV5 vectors when the pH was decreased to 4.5 (FIG. 8, pH 4.5-Int).

Example 9

This example illustrates the effects of varying pH on AAV6 distribution on cells subjected to TPP.

Figure 9:
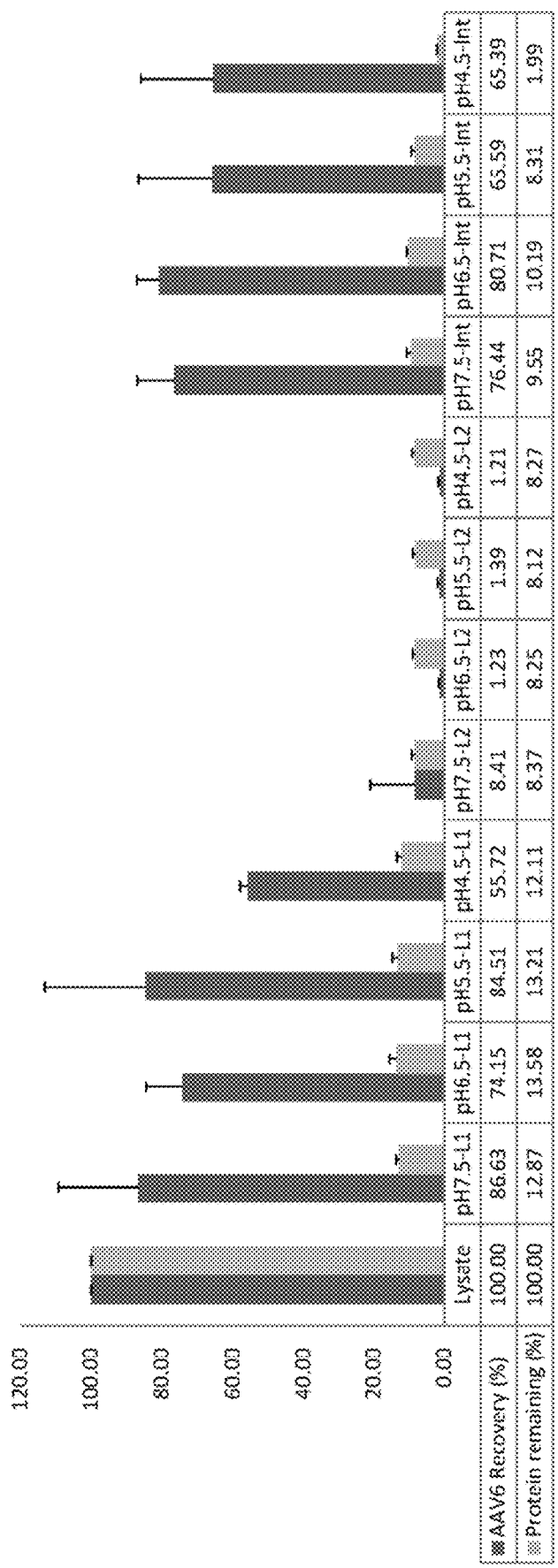
FIG. 9 illustrates the effects of different pH values on AAV6 vector recovery in a TPP method of the present teachings.

In these experiments, the pH conditions were varied in cell lysates for AAV6 purification in TPP. Cell lysates containing AAV6 vectors were prepared in Sf9 lysis buffer (pH 7.5) at 20% saturation of ammonium sulfate and then divided into 4 fractions. After incubation with nuclease for 1 hour at 37° C. to digest the cellular nucleic acids, ammonium sulfate was added to 20% saturation and each lysate was divided into 4 equal fractions. Three lysate fractions were adjusted to pH 6.5, pH 5.5, and pH 4.5 respectively with acetic acid, the fourth fraction was used to test the lysate at pH 7.5. All the lysates were then subjected to two rounds of TPP, and the AAV6 titers were then determined. The results are shown in FIG. 9. In FIG. 9, L1 represents the aqueous phase after first round of TPP at fixed 20% ammonium sulfate saturation; L2 represents the aqueous phase after second round of TPP at fixed 35% ammonium sulfate saturation; Int represents the interphase after a second round of TPP.

The majority of AAV6 vectors were recovered in the interphase in all pH values tested, but pH 6.5 showed the greatest AAV6 recovery rate (FIG. 9, pH 6.5-Int). Protein assays were performed to monitor the cellular protein removal at different pH values. The results indicate that as pH values decreased, more cellular proteins were removed. More than 95% cellular proteins were removed from the AAV6 samples when the cell lysates were adjusted to pH 4.5 (FIG. 9, pH 4.5-Int).

Example 10

This example illustrates visualization of the purification process using TPP methods of the present teachings.

Figure 10:
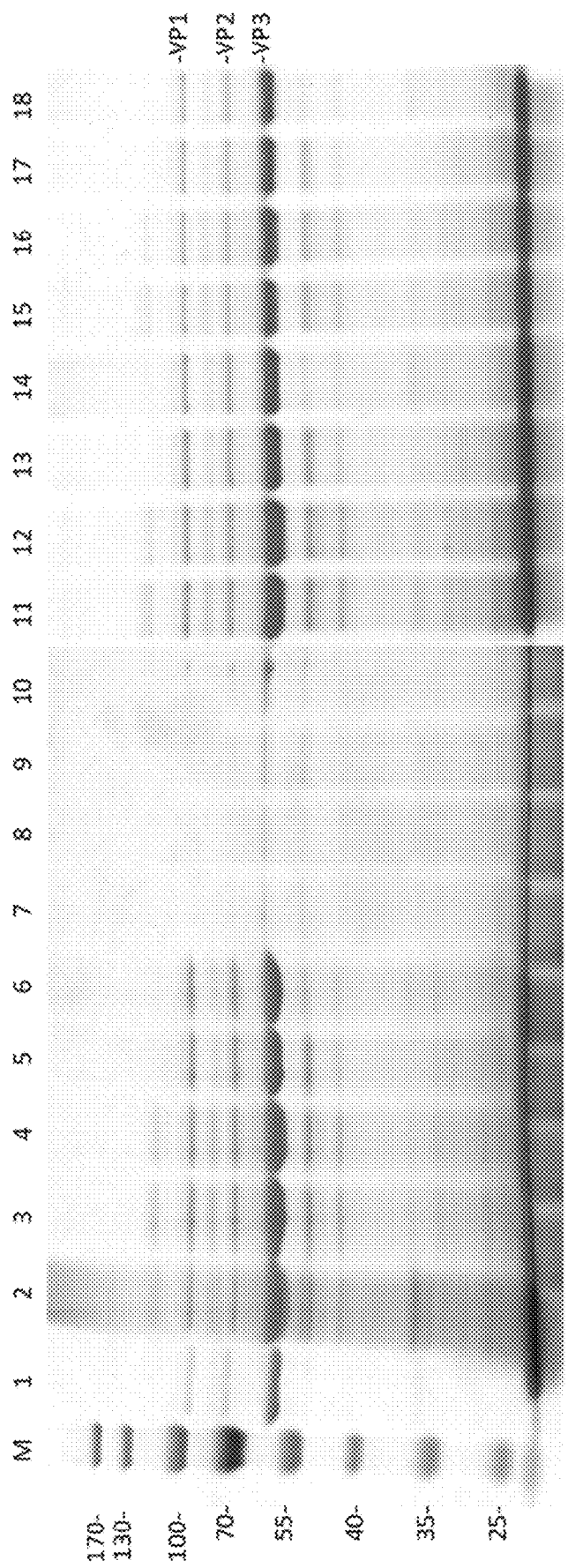
FIG. 10 illustrates a representative SDS-PAGE analysis of AAV samples collected from a TPP method of the present teachings.

SDS-PAGE analysis was performed to monitor the purification process using the TPP methods at different pH values. The gels were stained with the Simply Blue Staining kit. A representative SDS-PAGE image is shown in FIG. 10. The lanes are labelled as follows: lane M, protein ladders; lane 1, purified AAV9 vector as control; lane 2, cell lysate; lanes 3-6, aqueous phases from first round of TPP at pH 7.5, 6.5, 5.5, and 4.5; lanes 7-10, aqueous phases from second round of TPP at pH 7.5, 6.5, 5.5, and 4.5; lanes 11-14, interphases at pH 7.5, 6.5, 5.5, and 4.5 after the second round of TPP; lanes 15-18 contain the same samples as lanes 11-14 but with 50% less sample loaded onto the gel. FIG. 10 illustrates that after two rounds of TPP, the majority of cellular proteins were removed and clear AAV2 capsid proteins VP1, VP2, and VP3 were observed (see fractions 15, 16, 17, and 18, indicated at right).

Example 11

This example illustrates a large-scale preparation of AAV5 vectors.

Figure 11:
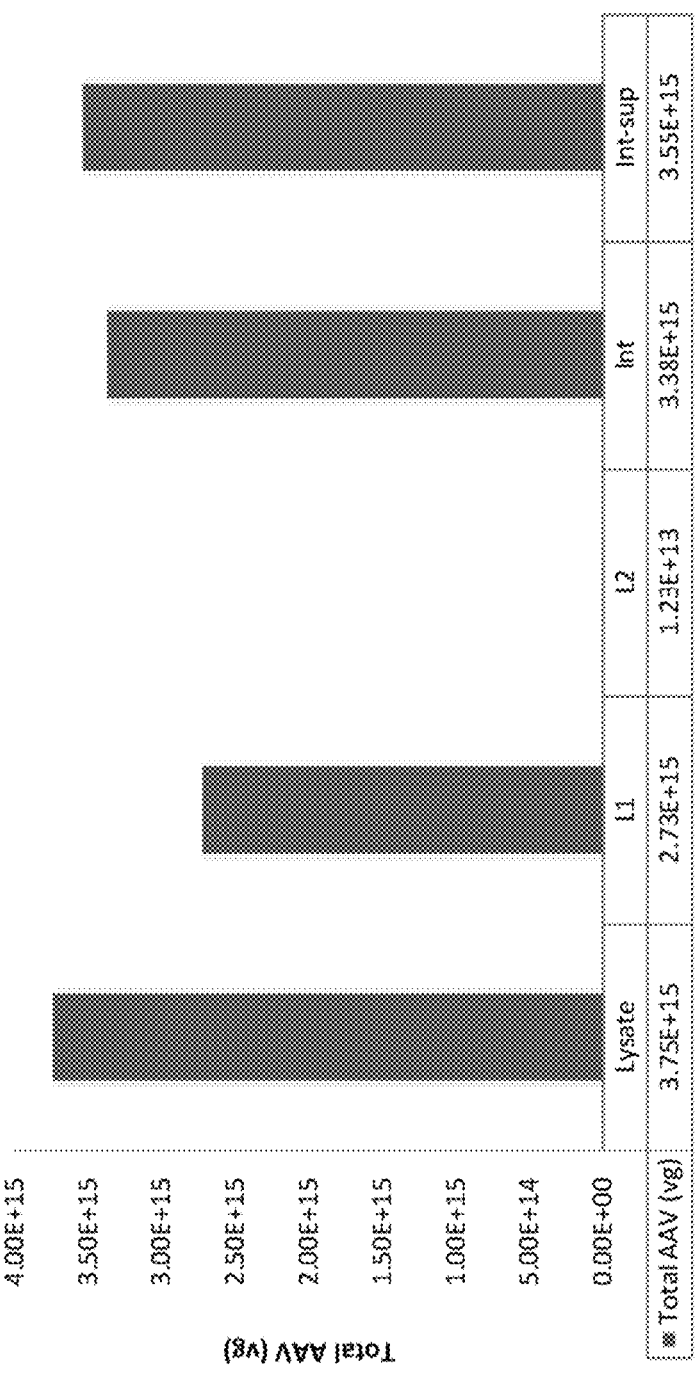
FIG. 11 illustrates a large scale purification of AAV5-Luciferase using a TPP method of the present teachings.

In these experiments, three liters of Sf9 cell culture were double-infected with rBV-inCapS-inRep and rBV-CMV-Luciferase, then cultured and lysed as described supra. The AAV5 vectors were then purified from the lysates using the 2-round TPP method of the present teachings. The results are shown in FIG. 11. In FIG. 11, L1 represents the aqueous phase after the first round of TPP at 20% saturation of ammonium sulfate; L2 represents the aqueous phase after the second round of TPP at 35% saturation of ammonium sulfate; Int, represents the interphase after the second round of TPP; Int-sup represents the supernatant harvested after centrifugation of Int at 10322×g for 20 min. Up to 3.55e+15vg of AAV5 vectors (95%) were recovered from a 3-liter cell culture after TPP purification.

Example 12

This example illustrates a large-scale preparation of AAV2 vectors.

Three liters of Sf9 cell culture are double-infected with rBV-inCap2-inRep and rBV-CMV-Luciferase and cultured and lysed as described supra. The AAV2 vectors are then purified from the lysates using two rounds of TPP in accordance with methods of the present teachings.

Example 13

This example illustrates a large scale preparation of AAV6 vectors.

Three liters of Sf9 cell culture are double-infected with rBV-inCap6-inRep and rBV-CMV-Luciferase and cultured and lysed as described in Materials and methods. The AAV6 vectors are then purified from the lysates using two rounds of TPP in accordance with methods of the present teachings.

Example 14

This example illustrates purification of AAV2 particles using TPP and column chromatography.

An AAV2 cell lysate is subjected to one round of TPP. The aqueous L1 phase is then further purified using MUSTANG® S and MUSTANG® Q (Pall Corporation, Port Washington, N.Y.) membrane coins according to Manufacturer's protocol. Briefly, the MUSTANG® S and Q coins are treated with 10 mL of 1 M NaOH followed by 10 mL of 1 M NaCl and 10 mL of 20 mM Tris-HCl (pH 9.0). 5 mL of the purified AAV are then desalted using PD-10 desalting columns and diluted 1:10 with 20 mM Tris-HCl (pH 9.0). This diluted solution is then applied to the MUSTANG® S coin. The flow-through is collected and applied to a MUSTANG® Q coin. After washing with 1.5 mL of 20 mM Tris-HCl (pH 9.0), the AAV particles are then eluted with elution buffer (20 mM Tris-HCl (pH 9.0), 300 mM NaCl), and desalted with PD-10 desalting columns. Titers are then measured with QPCR.

Example 15

This example illustrates purification of AAV6 particles using TPP and column chromatography.

An AAV6 cell lysate is subjected to one round of TPP. The aqueous L1 phase is then further purified using MUSTANG® S and MUSTANG® Q (Pall Corporation, Port Washington, N.Y.) membrane coins according to Manufacturer's protocol. Briefly, the MUSTANG® S and Q coins are treated with 10 mL of 1 M NaOH followed by 10 mL of 1 M NaCl and 10 mL of 20 mM Tris-HCl (pH9.0). 5 mL of the one round TPP-purified AAV6 sample is then desalted with PD-10 desalting columns and diluted 1:10 with 20 mM Tris-HCl (pH 9.0). This diluted solution is then applied to the MUSTANG® S coin. The flow-through is collected and applied to the MUSTANG® Q coin. After washing with 1.5 mL of 20 mM Tris-HCl (pH 9.0), the AAV particles is eluted with elution buffer (20 mM Tris-HCl (pH 9.0), 300 mM NaCl), and desalted with PD-10 desalting columns. AAV6 titers are then measured with a QPCR assay.

Example 16

This example illustrates a combination of one round of TPP followed by density gradient centrifugation to purify AAV2 particles An AAV2 cell lysate is subjected to a first round of TPP. The aqueous L1 phase is loaded onto the top of a step gradient with 1.55 g/cc and 1.32 g/cc of CsCl solutions and centrifuged at 28,000 rpm overnight (~20 hours). AAV2 particles are then collected with a syringe, then desalted with PD-10 desalting columns. AAV2 titers are then determined with a QPCR assay.

Example 17

This example illustrates purification of AAV5 by a combination of one round of TPP followed by density gradient centrifugation.

An AAV5 cell lysate is subjected to a first round of TPP. The aqueous L1 phase is loaded onto the top of a step gradient comprising 1.55 g/cc and 1.32 g/cc of CsCl solutions, and centrifuged at 28,000 rpm overnight (~20 hours). AAV5 particles are collected with a syringe, and desalted with PD-10 desalting columns. AAV5 titers are then determined using QPCR.

Example 18

This example illustrates purification of AAV6 particles by a combination of one round of TPP followed by density gradient centrifugation.

An AAV6 cell lysate is subjected to a first round of TPP. The aqueous L1 phase is loaded onto the top of a step gradient with 1.55 g/cc and 1.32 g/cc of CsCl solutions and centrifuged at 28,000 rpm overnight (~20 hours). AAV2 particles are collected with a syringe, desalted with PD-10 desalting columns and then the titers are determined with QPCR.

Example 19

This example illustrates infectivity of AAV2 particles purified by two rounds of TPP in accordance with the present teachings, and compared to two rounds of density gradient centrifugation.

In these experiments, two sets of AAV2 particles harboring a luciferase reporter gene were prepared side-by-side: one set was purified by performing two rounds of density gradient centrifugation with CsCl; the other set was purified using two rounds of TPP as described supra. Equal amounts of AAV2 particles were used to transduce HEK293 cells for three days according to Virovek's protocol (Chen, H., Mol. Ther. Nucleic Acids, 2012, 1, e57), and light-emitting cells were then scored. The results shown in Table 1 demonstrate that TPP-purified AAV2 particles infect at least as well as those prepared by standard methods.

Example 20

This example illustrates infectivity of AAV5 particles purified by two rounds of TPP in accordance with the present teachings, compared to two rounds of density gradient centrifugation.

In these experiments, two sets of AAV5 particles harboring a luciferase reporter gene were prepared side-by-side: one set was purified by performing two rounds of density gradient centrifugation with CsCl; the other set was purified using two rounds of TPP as described supra. Equal amounts of AAV5 particles were used to transduce HEK293 cells for three days according to Virovek's protocol (Chen, H., Mol. Ther. Nucleic Acids, 2012, 1, e57), and light-emitting cells were then scored. The results shown in Table 1 demonstrate that TPP-purified AAV5 particles infect at least as well as those prepared by standard methods.

Example 21

This example illustrates infectivity of AAV6 particles purified by two rounds of TPP in accordance with the present teachings, compared to two rounds of density gradient centrifugation.

In these experiments, two sets of AAV6 particles harboring a luciferase reporter gene were prepared side-by-side: one set was purified by performing two rounds of density gradient centrifugation with CsCl; the other set was purified using two rounds of TPP as described supra. Equal amounts of AAV6 particles were used to transduce HEK293 cells for three days according to Virovek's protocol (Chen, H., Mol. Ther. Nucleic Acids, 2012, 1, e57), and light-emitting cells were then scored. The results shown in Table 1 demonstrate that TPP-purified AAV6 particles infect at least as well as those prepared by standard methods.

TABLE 1

Comparison of infectivity of AAV vectors purified by CsCl or TPP methods.

| Sample | Description[a] | Green Intensity Value[b] | Infectivity Ratio[c] |
|---|---|---|---|
| 1. | AAV2-CMV-GFP, CsCl purified | 71.567 | 0.84 |
| 2. | AAV2-CMV-GFP, TPP purified | 85.181 | 1.00 |
| 3. | AAV5-CMV-GFP, CsCl purified | 27.906 | 0.93 |
| 4. | AAV5-CMV-GFP, TPP purified | 29.871 | 1.00 |
| 5. | AAV6-CMV-GFP, CsCl purified | 27.990 | 0.85 |
| 6. | AAV6-CMV-GFP, TPP purified | 33.064 | 1.00 |

[a] AAV vectors of 1.5e+9 vg/well were added to each well with 1 5e+5 cells for 3 days.
[b] Green intensity value was measured on the whole optical field with free-software ImageJ (NIH)
[c] The higher intensity value of each pair of AAV vectors was set to 1. All publications cited herein are hereby incorporated by reference, each in its entirety.

What is claimed is:

1. A method of purifying an adeno-associated virus from a baculovirus-infected cell lysate, the method comprising:
   a) forming a first mixture comprising i) an aqueous phase comprising water and a cell lysate comprising an adeno-associated virus, ii) t-butanol, and iii) ammonium sulfate at a first concentration;
   b) separating the first mixture to form a first organic phase, a first interphase, and a first aqueous phase; and
   c) collecting the first aqueous phase, wherein the ammonium sulfate at a first concentration is ammonium sulfate at a concentration at which t-butanol is immiscible with water.

2. A method in accordance with claim 1, wherein the adeno-associated virus is selected from the group consisting of AAV2, AAV5 and AAV6.

3. A method in accordance with claim 1, wherein the first ammonium sulfate concentration is from 10% to 30% saturation.

4. A method in accordance with claim 1, wherein the adeno-associated virus is an AAV2 and the first ammonium sulfate concentration is from 10% to 25% saturation.

5. A method in accordance with claim 1, wherein the adeno-associated virus is an AAV5 and the first ammonium sulfate concentration is from 10% to 20% saturation.

6. A method in accordance with claim 1, wherein the adeno-associated virus is an AAV6 and the first ammonium sulfate concentration is from 15% to 30% saturation.

7. A method in accordance with claim 1, wherein the separating the first mixture comprises settling the first mixture for at least 30 minutes.

8. A method in accordance with claim 1, wherein the separating the first mixture comprises centrifuging the first mixture.

9. A method in accordance with claim 1, further comprising:
   d) forming a second mixture comprising i) the first aqueous phase collected in c), ii) t-butanol, and iii) ammonium sulfate at a second concentration in which t-butanol is immiscible with water;
   e) separating the second mixture to obtain a second organic layer, a second interphase, and a second aqueous layer; and
   f) collecting the second interphase.

10. A method in accordance with claim 9, wherein the second ammonium sulfate concentration is from 25% to 40% saturation.

11. A method in accordance with claim 9, wherein the adeno-associated virus is an AAV2 and the second ammonium sulfate concentration is from 35% to 40% saturation.

12. A method in accordance with claim 9, wherein the adeno-associated virus is an AAV5 and the second ammonium sulfate concentration is from 35% to 40% saturation.

13. A method in accordance with claim 9, wherein the adeno-associated virus is an AAV6 and the second ammonium sulfate concentration is from 30% to 35% saturation.

14. A method in accordance with claim 9, wherein the separating the second mixture comprises settling the second mixture for about 30 to about 60 minutes.

15. A method in accordance with claim 9, wherein the separating the second mixture comprises centrifuging the second mixture.

16. A method in accordance with claim 1, wherein the cell lysate comprising an adeno-associated virus is a lysate of an insect cell comprising a virus.

17. A method in accordance with claim 16, wherein the insect cell comprising an adeno-associated virus is an Sf9 cell comprising the adeno-associated virus.

18. A method in accordance with claim 16, wherein the insect cell comprising an adeno-associated virus is an Sf9 cell comprising an AAV.

19. A method in accordance with claim 1, wherein the cell lysate comprising an adeno-associated virus is a lysate of a mammalian cell comprising the adeno-associated virus.

20. A method in accordance with claim 19, wherein the mammalian cell comprising the adeno-associated virus is an HEK293 cell comprising the adeno-associated virus.

21. A composition comprising:
   a cell lysate comprising an adeno-associated virus;
   ammonium sulfate; and
   t-butanol wherein the ammonium sulfate is at a concentration in which t-butanol is immiscible with water.

22. A composition in accordance with claim 21, wherein the adeno-associated virus is selected from the group consisting of an AAV2, an AAV5 and an AAV6.

23. A composition in accordance with claim 21, wherein the cell lysate comprising an adeno-associated virus is a cell lysate of an insect cell comprising an adeno-associated virus.

24. A composition in accordance with claim 21, wherein the cell lysate comprising an adeno-associated virus is a cell lysate of a mammalian cell comprising an adeno-associated virus.

* * * * *